US007608552B2

(12) United States Patent
Meyer et al.

(10) Patent No.: US 7,608,552 B2
(45) Date of Patent: Oct. 27, 2009

(54) DENTAL MATERIAL OR PRODUCT AND METHOD OF FORMING A DENTAL PRODUCT

(75) Inventors: Gerhard Meyer, Wesel (DE); Thomas Conrad, Dortmund (DE)

(73) Assignee: Chemichl AG, Vaduz (DE)

( * ) Notice: Subject to any disclaimer, the term of this patent is extended or adjusted under 35 U.S.C. 154(b) by 0 days.

(21) Appl. No.: 10/748,084

(22) Filed: Dec. 30, 2003

(65) Prior Publication Data

US 2004/0168610 A1 Sep. 2, 2004

(30) Foreign Application Priority Data

Dec. 30, 2002 (DE) ............................... 102 61 720

(51) Int. Cl.
*C04B 35/486* (2006.01)
*C04B 35/111* (2006.01)
*A61K 6/00* (2006.01)
(52) U.S. Cl. ..................... 501/103; 501/104; 501/127; 106/35
(58) Field of Classification Search ................ 501/1, 501/103, 152, 104, 127; 106/35
See application file for complete search history.

(56) References Cited

U.S. PATENT DOCUMENTS

| 4,626,392 | A | * | 12/1986 | Kondo et al. | ................ | 264/643 |
| 4,748,138 | A | * | 5/1988 | Watanabe et al. | ............ | 501/87 |
| 4,820,666 | A | * | 4/1989 | Hirano et al. | ............... | 501/104 |
| 4,978,640 | A | * | 12/1990 | Kelly | ........................... | 501/32 |
| 5,376,442 | A | * | 12/1994 | Davidson et al. | .......... | 428/307.7 |
| 5,723,393 | A | | 3/1998 | Majumdar et al. | .......... | 501/104 |
| 5,824,089 | A | * | 10/1998 | Rieger | ....................... | 424/423 |
| 5,863,850 | A | * | 1/1999 | Nawa et al. | ................. | 501/105 |
| 6,087,285 | A | * | 7/2000 | Oomichi et al. | ............ | 501/103 |
| 6,165,925 | A | * | 12/2000 | Rieger | ....................... | 501/103 |
| 6,201,038 | B1 | * | 3/2001 | Waller et al. | ................ | 523/109 |
| 6,358,874 | B1 | * | 3/2002 | Kobayashi et al. | ......... | 501/105 |
| 6,455,029 | B1 | * | 9/2002 | Angeletakis et al. | ......... | 424/49 |
| 6,796,143 | B2 | | 9/2004 | Clasen et al. | ................ | 65/17.3 |
| 7,012,036 | B2 | * | 3/2006 | Nawa et al. | ................. | 501/105 |
| 7,056,851 | B2 | * | 6/2006 | Nawa | ......................... | 501/105 |
| 2002/0006532 | A1 | * | 1/2002 | Robin | ......................... | 428/697 |
| 2002/0026810 | A1 | * | 3/2002 | Clasen et al. | ............... | 65/17.6 |
| 2002/0071813 | A1 | * | 6/2002 | Angeletakis et al. | ......... | 424/49 |
| 2002/0193462 | A1 | * | 12/2002 | Angeletakis et al. | ........ | 523/115 |

FOREIGN PATENT DOCUMENTS

| CA | 2 380 576 | | 2/2001 |
| DE | 101 20 084 | | 10/2002 |
| EP | 435677 | * | 9/1992 |
| EP | 1 195 360 A1 | | 4/2002 |
| WO | WO 01/12097 A1 | | 2/2001 |

OTHER PUBLICATIONS

O'Bannon, Dictionary of Ceramic Science and Engineering, 1984, pp. 54-55, 101.*
The Condensed Chemical Dictionary, Haw;ey (1974)pp. 183, definition of ceramic.*
Wikpedia, (2007), Definition of Ceramic, 7 pages.*
"Monodispersed Metal (Hydrous) Oxides—A Fascinating Field of Colloid Science", Matijevic, Acc. Chem. Res., 1981, pp. 22-29.
Formation, Packing, and Sintering of Monodisperse $TiO_2$ Powders, Barringer et al., J. Am .Ceram. Soc. 1982, pp. C199-C201.
"Applications of Sol-Gel Methods for Glass and Ceramics Processing", Mackenzie, Ultrastructure Processing of Ceramics, Glasses and Composites, 1984, pp. 15-26.
"Synthesis and Characterization of Monosized Doped $TiO_2$ Powders", Fegley Jr. et al., J. Am .Ceram. Soc. 1984, pp. C113-C116.
"Synthesis, Characterization, and Processing of Monosized Ceramic Powders", Fegley et al., Mat., Res. Soc. Symp. Proc. Vol. 32, 1984, pp. 187-197.
"Preparation of Y-Doped Zirconia by Emulsion Technique", Rinn et al., Ceramic Powder Processing Science (Proceedings of the Second International Conference, Oct. 12-14, 1988, pp. 221-228.
"Herstellung Nanoskaliger Pulver Durch Thermische Synthese im Pulsationsreaktor", Begand et al., 1988, D-12-D-16.
"Einsatz des Pulsationsreaktors für die Stoffbehandlung in der Chemischen Industrie", Begand et al, 1988, pp. 746-749.
"Processing of Nanosized Ceramic Powders—A Bimodal Slip Casting Approach", Bowen et al., Ceramic Transactions, 1988, pp. 211-218.
"Preparation of Monodisperse $ArO_2$ by the Microwave Heating of Zirconyl Chloride Solutions", Moon et al., J. Am. Ceram. Soc. 78[4], 1995, pp. 1103-1106.
"Sintering of Bimodal $Y_2O_3$-Stabilized Zirconia Powder Mixtures with a Nanocrystalline Component", Moskovits et al., NanoStructured Materials, vol. 11, No. 2, 1999, pp. 179-185.
"Sintering of Bimodal Alumina Powder Mixtures with a Nanocrystalline Component", Ravi et al. NanoStructured Materials, vol. 11, No. 7, 1999, pp. 853-859.
Encyclopedia Chemie of Brockhaus, vol. 1/A-K pp. 565-566.
Search Report in EP 03 02 8804 dated Apr. 6, 2006.
"What Exactly is Particle Size and Particle Shape?" http://www.malvern.co.uk/LabEng/products/iwtm/particle_size_particle_shape.htm, 2 pages, printed Mar. 27, 2007.
Entry for "oxide" from Lexikon der Chemie, Spektrum Akademischer Verlag (Encyclopedia of Chemistry, Spectrum Academic Publishing House), pp. 449-450, and English-language translation thereof, 5 pages total (1998).
Entry for "ceramic" from Chemie chemical encyclopedia, VEB F.A. Brockhaus Publishing House, pp. 565-566, and English-language translation thereof, 5 pages total (1971).

* cited by examiner

*Primary Examiner*—Karl E Group
(74) *Attorney, Agent, or Firm*—Marshall, Gerstein & Borun LLP

(57) ABSTRACT

The disclosure relates to metal oxide powders with a bimodal particle size distribution, to ceramics that can be made from these metal oxide powders, especially milling ceramics for use in dental technology, to a method for the production of the metal oxide powders and of the ceramics, to the use of nanoscale metal oxide powders for the production of the metal oxide powders and of the ceramics as well as to dental ceramic products.

16 Claims, No Drawings

DENTAL MATERIAL OR PRODUCT AND METHOD OF FORMING A DENTAL PRODUCT

BACKGROUND OF THE INVENTION

1. Field of the Invention

The invention relates to metal oxide powders with a bimodal particle size distribution or to bimodal ceramic-binder material composites, to ceramics that can be made from these metal oxide powders or composites, especially milling ceramics for use in dental technology, to methods for producing of the metal oxide powders and of the ceramics, to the use of nanoscale metal oxide powders for producing the metal oxide powders and of the ceramics, and to dental ceramic products.

2. Related Technology

Ceramics made of metal oxide powders, especially $Al_2O_3$, have been in use for some time in dental technology because of their stability under load and their biocompatibility. Partially stabilized $ZrO_2$ has also been considered since, due to its polymorphic state, it has greater mechanical strength than $Al_2O_3$. These ceramics are processed by means of a milling cutter, whereby either a green compact, a pre-sintered body, a final-sintered porous body (with subsequent glass infiltration), or a final-sintered solid ceramic body is subject to machining. To start with, the metal oxide powders are compacted under pressure. For this purpose, cold isostatic or uniaxial pressing methods are commonly employed, whereby, due to the inevitable density gradient in comparison to the CIP (cold isostatic pressing) process, uniaxial pressing does not allow a uniform density.

As an alternative to this production of green compacts, companies in the dental industry, for example, Metoxit, supply ceramic blocks treated by a hot isostatic process. Here, the ceramic starting powder is simultaneously compacted and sintered. This results in the highest compacting which, at 6.065 g/cm$^3$, comes close to the theoretical density in the case of, for example, $ZrO_2$ doped with 3 mole-% of $Y_2O_3$. However, this method is very costly and it yields ceramic blocks that, due to their high density, can take up to six hours to be made into a finished three-part dental bridge in a milling process, for instance, using a dental milling cutter made by the DCS Company.

Dentsply Degussa Dental offers an alternative method. Here, the compacted green compact is first machined, taking into account a margin for shrinkage, and it subsequently undergoes final sintering. However, milling the green compact encounters problems because of the relatively low green density of monomodal powders since fractures can often occur during machining. Shipping the green compacts to dental laboratories that will process them is problematic because of their non-optimal green density. Furthermore, due to the great shrinkage, it is also problematic to set a deviation from the isotropic shrinkage that is still acceptable for dental requirements. Furthermore, the high sintering temperature and the long sintering duration have proven to be disadvantageous for practical use since, for example, these factors lead to greater stress and greater thermal wear of the heating elements, or else expensive types of furnaces must be used.

The low shrinkage of the bimodal metal oxide powder according to the invention also allows a better setting of an approximately isotropic shrinkage, especially of free-form surfaces. Moreover, the greater packing density accounts for lower shrinkage, as a result of which the green compacts take up less space during transportation as well as in the sinter furnace. If need be, the sintering temperature can also be lowered, without detrimentally diminishing the strength of the product to a level below that required for dental applications.

The In-Ceram method of the Vita Company includes the production of final-sintered porous ceramic blocks that can also be machined using low-power dental milling cutters. In order to attain the strength needed for use, the porous body is infiltrated with lanthanum glass, whereby the infiltration temperature lies below the sintering temperature of the porous final-sinter ceramic body and, consequently, shrinkage is almost completely avoided. The problems encountered here are the quite low strength of the porous final-sinter ceramic body (limited handling) as well as the non-optimal strength of the ceramic-glass composite after the infiltration. Doping with nanoscale ceramic powder brings about an increase in strength of the porous final-sinter ceramic block that functions as the skeleton.

In order to lower the sintering temperature during the production of dental milling ceramics, it has been proposed to use so-called nanoscale metal oxide powders, that is to say, metal oxide powders, whose average particle sizes lie in the nanometer range instead of the usual metal oxide powders whose particle sizes are greater than 1 μm. However, the handling and processing of these "nano-powders" have proven to be difficult in actual practice. Thus, their high sintering activity can cause undesired agglomeration and increased grain growth. Moreover, the low bulk density or tap density often renders the shaping procedure difficult. Consequently, there is so much technical effort involved in creating a nanoscale structure that satisfactory profit margins cannot be attained on the dental market. Furthermore, the use of pure nanoscale metal oxide powders is not feasible due to their high production costs. A special effect of a nanoscale structure, however, has proven to be very advantageous for the dental industry. If the particle boundary range of the structure of the sintered sample is below ½₀ of the wavelength of visible light, then it will be transparent. In actual practice, among other things, a particle size that lies below the wavelength of visible light leads to a more or less pronounced translucence. This translucence is also improved by especially chemically pure starting materials, since, for example, no impurities can become deposited on the skeleton ceramic. In dental practice, greater translucence of the skeleton ceramic means that a thinner ceramic layer is needed which, on the one hand, makes it easier to achieve optimal esthetics and, on the other hand, brings about less abrasion of the natural teeth that serve to anchor a dental bridge.

SUMMARY OF THE INVENTION

Therefore, it is an objective of the invention to provide a metal oxide powder or a ceramic-binder composite that, on the one hand, exhibits the best possible resistance against transportation and handling damage and that, on the other hand, is suitable for the production of a ceramic that can undergo optimal milling processing (optimal green density), if possible before its final sintering, and in the process—also with a considerable reduction of the sintering temperature and substantial shortening of the sintering duration—ends up having an adequate strength and the best possible translucence.

DETAILED DESCRIPTION

This objective is achieved by a bimodal metal oxide powder or bimodal ceramic-binder composite, comprising
(a) a first metal oxide powder; and
(b) a second, nanoscale metal oxide powder;
wherein the first metal oxide powder (a) has a $d_{50}$ value of 0.2 μm to 12 μm; and
the second, nanoscale metal oxide powder (b) has a $d_{50}$ value ranging from 10 nm to 300 nm, wherein the ratio of the $d_{50}$ values of (a) to (b) lies at a maximum of 40 to 1.

The second metal oxide provides highly sintering-active, and either of the first and second metal oxide powders may or may not have surface modification(s). The quantity ratio of (a) to (b) is generally from 0.1:99.9 to 99.9 to 0.1.

In the state of the art, metal oxide powder combinations have been studied as follows. M. Moskovits, B. G. Ravi and R. Chaim, in NanoStructured Materials, Vol. 11, No. 2, pp. 179-185, the entire disclosure of which is incorporated by reference herein, studied a bimodal powder whose nano-component had an average particle size of 10 nm and whose base component had an average particle size of 430 nm. With a size ratio of both components of over 40, and especially with such a fine nano-component, the production of a homogeneous powder mixture with an acceptable amount of technical effort is only possible to a limited extent. Assuming an ideal spherical shape of the base component, the optimization of the packing density can only be achieved by large agglomerates of the nanoscale component, as a result of which a nano-component is no longer present in actual fact.

P. Bowen et al., Ceramic Transactions (1988), pp. 211-218, the entire disclosure of which is incorporated by reference herein, studied the compacting behavior of bimodal $\gamma$-$Al_2O_3$ powders, whereby the shaping was done by means of slip casting or cold isostatic pressing. The particle size of the coarser powder was 1 µm, whereas that of the nano-powder was 70 nm to 120 nm. After the sintering, a particle size of about 1 µm was found. In the bimodal $Al_2O_3$ powders or $Al_2O_3$-binder composites according to the invention, preferably allotrophic modifications of $Al_2O_3$ are used as the coarser constituent.

It is also possible to use transition alumina such as mixed types having an oxidic, oxide-hydrate composition that can also contain hydroxyl groups and differently chemically bound water. Preferably, however, alpha and gamma alumina is used. The results do not yield a clear-cut picture. Although a cold-isostatic compacting yields the highest green density, it also leads to a very low sintered density and this was even higher with the monomodal $\gamma$-$Al_2O_3$ powder. The use of such a powder as a milling ceramic in dental technology is thus ruled out. Consequently, bimodal metal oxide powders made of $\gamma$-$Al_2O_3$, consisting of a first $\gamma$-$Al_2O_3$ powder having an average particle size of 1 µm and of a second $\gamma$-$Al_2O_3$ powder having an average particle size of 70 nm to 120 nm, as were described by Bowen et al., are excluded from the bimodal metal oxide powders according to the invention. Concerning the use of the metal oxide powders according to the invention in ceramics, especially in milling ceramics, or their production as well as their use in dental products, these can also be made of bimodal metal oxide powders according to the invention from $\gamma$-$Al_2O_3$, consisting of a first $\gamma$-$Al_2O_3$ powder having an average particle size of 1 µm and of a second $\gamma$-$Al_2O_3$ powder having an average particle size of 70 nm to 120 nm, whereby preference is given to the use of $\gamma$-$Al_2O_3$ powders.

The bimodal metal oxide powders according to the invention or the bimodal ceramic-binder composite according to the invention provide a metal oxide powder from which green compacts or pre-sinter ceramics can be produced that, before final sintering, can undergo milling processing without the occurrence of fractures or other flaws caused by machining and, after the subsequent final sintering, they have sufficient mechanical strength for use in dental technology. It has been found that ceramics that are made of the bimodal metal oxide powder according to the invention have a number of excellent properties.

The bimodal metal oxide powders are characterized in that they can be especially well integrated into production processes, and they are especially well-suited for use in plasma methods. Moreover, they have surprisingly good mechanical properties, and they are especially well-suited for processing by milling.

These ceramics have increased green compact strength so that, for example, the green compact ceramics obtained, for example, by means of cold isostatic compacting (or other pre-sinter ceramics that can be obtained by other methods) using the bimodal metal oxide powders according to the invention can be machined before and after final sintering and processed without fractures, as a result of which they are suitable for the production of dental ceramics that are as close as possible to the final dimensions. In addition to this, there is also the fact that these green compact ceramics or pre-sinter ceramics have a shrinkage of less than 15% during final sintering. In contrast, the green compact ceramics or pre-sinter ceramics made of conventional metal oxide powders known from the state of the art have a shrinkage of about 25% or more after final sintering. This can lead to a distortion of the ceramic and its dimensioning calls for larger milling tools. It has also been found that the final sintering temperature to be used for the final sintering of the ceramics that can be made from the bimodal metal oxide powders according to the invention lies considerably below the final sintering temperature needed for the ceramics made of conventional metal oxide powders. This translates into lower energy costs for the operation of the sinter furnace since the temperatures needed for the sintering are lower and the sintering process takes less time. Advantageously, existing types of furnaces found in dental laboratories for pressing ceramics can continue to be used.

It was completely surprising that the bimodal metal oxide powders according to the invention can be used to produce ceramics that have such a high translucence that entirely new horizons open up for dental technicians in terms of the esthetic design possibilities. In no instance was the translucence of a ceramic body containing the special nano-component less than the translucence of the base powder, whereas bimodal mixtures using nano-components made by means of flame pyrolysis or by means of sol-gel processes were always more opaque than the base powder. Therefore, their use as opto-ceramics also seems conceivable.

The ceramics that can be obtained from bimodal metal oxide powders according to the invention also have greater mechanical strength in comparison to the prior-art ceramics made of metal oxide powders without a nanoscale fraction, under the same sintering conditions, and this aspect has a positive effect on the service life of the ceramics.

The bimodal metal oxide powder according to the invention comprises, consists essentially of, or consists of a first metal oxide powder (a) with a $d_{50}$ value of 0.2 µm to 12 µm and of a second nanoscale metal oxide powder (b) with a $d_{50}$ value 10 nm to 300 nm. It is possible to make the first metal oxide powder out of a different metal oxide than the second, nanoscale metal oxide powder. Preferably, both metal oxide powders (a) and (b) are made of the same metal oxide. The metal oxides are preferably selected from the group consisting of undoped $ZrO_2$, or $ZrO_2$ doped with $CeO_2$, $CaO$, $MgO$, $Sc_2O_3$, or $Y_2O_3$ as well as $TiO_2$ and $Al_2O_3$. Special preference is given to $ZrO_2$ doped with $Y_2O_3$.

Examples of the first metal oxide powders (a) are commercially available metal oxide powders made, for example, by Tosoh, Alcoa, Auer-Remy, alusuisse martinswerk, Sumitomo, or Zirconia Sales. Normally, the first metal oxide powder is stabilized with another metal oxide (e.g., $Y_2O_3$). The other metal oxide powder is preferably present in an amount ranging from 0.5 mole-% to 12 mole-%, relative to the total amount of the first metal oxide (a). Especially suitable stabilizers have been found to include—aside from calcium oxide (CaO)—especially magnesium oxide (MgO) in an amount ranging from 7 mole-% to 12 mole-%, especially about 9 mole-%, of MgO or scandium oxide ($Sc_2O_3$), cerium oxide ($CeO_2$) or yttrium trioxide ($Y_2O_3$) in an amount of 1 mole-% to 5 mole-%, especially approximately 3 mole-% of $Y_2O_3$.

The second, nanoscale metal oxide powder (b) can be either unstabilized or else stabilized with another metal oxide. Suitable stabilizers include, among others, CaO, $Sc_2O_3$, $CeO_2$, MgO, and especially $Y_2O_3$. The other metal oxide powder is preferably present in an amount of 0.5 mole-% to 12 mole-%, relative to the total amount of the second, nanoscale metal oxide powder (b). The preferred yttrium trioxide ($Y_2O_3$) is especially present in an amount of 1 mole-% to 5 mole-%, especially approximately 3 mole-%, of $Y_2O_3$. $Al_2O_3$ and $TiO_2$ can also be used as nanoscale metal oxides.

The nanoscale metal oxide powders (b) used to produce the bimodal metal oxide powders according to the invention can be obtained by means of any suitable synthesis method. Thus, metal oxide powders can be made, for example, via various chemical routes by means of sol-gel synthesis. One method is the micro-emulsion technique set forth by G. Rinn and H. Schmidt in Ceramic Powder Processing Science (Proceedings of the Second International Conference, Oct. 12 to 14, 1988). Other possibilities are offered by Y. T. Moon, D. K. Kim, C. H. Kim in J. Am. Ceram. Soc., 78[4] 1103-106; J. D. Mackenzie in Ultrastructure Processing of Ceramics, Glasses and Composites, 1984, pp. 15-26; E. A. Barringer and H. K. Bowen in J. Am. Ceram. Soc., 1982, pp. 199-201; E. Matijevic in Acc. Chem. Res., 1981, pp. 22-29; Fegley and Barringer in Mat. Res. Soc. Proc., 1984, pp. 187-197. As an alternative, the metal salt sols can-yield the nanoscale metal oxide powders by means of flame pyrolysis according to S. Begand and S. Ambrosius in DKG, pp. D12-D16, 1988 and in Chemie Ingenieur Technik [chemical engineering technology], pp. 746-749; 1988. Finally, the nanoscale metal oxide powders can also be made by means of a plasma synthesis method according to German Patent Publication No. DE 33 39 490 A1.

The entire respective disclosure of each of the foregoing publications is incorporated by reference herein.

Surprisingly, it has been found that especially the addition of nanoscale metal oxide powder, preferably $ZrO_2$ and $Y_2O_3$-doped $ZrO_2$ and produced by means of plasma synthesis, yields especially good results, that is to say, especially low shrinkage, high sintered density, high bend strength, high translucence, etc. in the ceramic.

Moreover, it is preferred for the second, nanoscale metal oxide powder (b) to have an average particle size of 5 nm to 70 nm, especially from 14 nm to 56 nm and preferably from 40 nm to 50 nm.

Fundamentally, the content of the bimodal metal oxide powder according to the invention in the second, nanoscale metal oxide powder (b) is not limited upwards or downward when it comes to the above-mentioned desirable properties of the ceramics made thereof. However, it has been found that an especially low shrinkage, an especially good processability of the green compact, a good assurance of the isotropic shrinkage and the highest possible transparency of the ceramics with concurrent high mechanical strength can be achieved when the bimodal metal oxide powder according to the invention comprises 5% to 30% by weight, especially 10% to 25% by weight and preferably about 20% by weight, of the second, nanoscale metal oxide powder (b) (relative to the total weight of the bimodal metal oxide powder).

The best results were obtained with a bimodal $ZrO_2$ metal oxide powder that contains $ZrO_2$ stabilized with 3 mole-% of $Y_2O_3$ as the nanoscale metal oxide powder (b), the $ZrO_2$ having been made by means of a plasma synthesis method, in an amount of about 20% by weight (relative to the total weight of the bimodal metal oxide powder).

The bimodal metal oxide powders can be made in any suitable manner from their individual components. Preferably, they are made in such a way that (A) the first metal oxide powder (a) and the second, nanoscale metal oxide powder (b) are mixed together; and (B) the mixture produced in Step (A) is subjected to granulation.

As an alterative, the bimodal metal oxide powders according to the invention can also be made by means of a method in which (A') the first metal oxide powder (a) is subjected to granulation; and (B') the granules produced in Step (A') are mixed with the second, nanoscale metal oxide powder (b).

(A) or else (B') can be mixed either in the dry state or in the presence of a suitable organic solvent, for example, an alcohol such as ethanol. By adding suitable surface-active modifiers (among others, surfactants, e.g. Tegotens T826), an improved deagglomeration to the primary particle size occurs as well as a chemical modification of the particle surfaces that is important for the further processing and product quality.

Normally, the mixing is carried out under agitation for about 2 hours to 16 hours, especially for 8 hours to 12 hours, and particularly preferably for about 10 hours.

Another subject matter of the invention is a ceramic with bimodal particle distribution that can be made from a bimodal metal oxide powder according to the invention, comprising (a) a first metal oxide powder (a) with a $d_{50}$ value of 0.2 μm to 12 μm and (b) a second, nanoscale metal oxide powder with a $d_{50}$ value of 10 nm to 300 nm with (c) a size ratio of the $d_{50}$ values of (a) to (b) of 40 to 1 at the maximum.

The ceramics that can be made from the bimodal metal oxide powders according to the invention generally have a bimodal particle size distribution, whereby (1) a first phase comprises a metal oxide having an average particle size of at least 250 nm; and (2) a second phase comprises a metal oxide having an average particle size of 25 nm to 250 nm.

The ceramics according to the invention are preferably, among other things, green compacts or pre-sinter ceramics; especially preferably, the ceramics according to the invention are milling ceramics. Due to their low shrinkage, even before undergoing their final sintering, these compacted ceramics can also be machined in already existent milling systems, especially dental milling systems, that until now have only milled completely sinter ceramics, that is to say, ceramics that have undergone final sintering. For the purposes of dental technology, these ceramics can subsequently be sintered to make a dental ceramic product having the appropriate dimensions, for example, a dental crown or dental bridge. Of course, the ceramics according to the invention can also first undergo final sintering before they are further processed. The production of a final-sintered, porous ceramic that can be subjected to infiltration is improved by the ceramic according to the invention since the porous skeleton material has improved mechanical properties.

The green compact ceramics of the invention or the pre-sinter ceramics are normally produced by means of suitable methods in that the bimodal metal oxide powder that can be obtained by means of the methods described above (C) undergoes cold isostatic final compacting or else it is first pre-compacted and then undergoes final compacting and (C') is subjected to a pre-sintering (sintering temperature: 300° C. to 1200° C. [572° F. to 2192° F.]; sintering duration: 0.5 hour to 8 hours).

The cold isostatic compacting of the bimodal metal oxide powder according to the invention is carried out, for example, batchwise by means of the co-called wet-bag method in a CIP installation made by Phi Technologies at a compacting pressure of 200 MPa to 1000 MPa, preferably approximately 300 MPa. As an alternative, especially taking into account the production of green compacts in large numbers, the compacting can also be carried out by means of cold isostatic compacting by means of the dry-bag method or else uniaxially.

In particular, a pre-compacting with subsequent grinding of the green compact and a subsequent final compacting is also possible. Moreover, further processing by means of HIP (hot isostatic pressing) is also possible. The ceramic obtained in this manner can then be subjected to sintering in another process step (D) before the further processing continues. As an alternative and especially preferably, the compacted green compact undergoes a milling process in a process step (E) before the milling ceramic thus obtained is subjected to sintering in a further step (D'). The sintering is carried out in conventional sinter furnaces, e.g. bottom-loading furnaces, at temperatures ranging from 900° C. to 1700° C. [1652° F. to 3092° F.], preferably at about 1300° C. [2372° F.]; the sintering duration is normally about 0.5 hour to 20 hours, preferably 1 hour to 4 hours. Due to the special properties of the bimodal metal oxide powders according to the invention from which the ceramics according to the invention can be made, their processing in dental technology can be done extremely close to the final dimensions.

The ceramics according to the invention are consequently used mainly as milling ceramics, especially as dental milling ceramics, without being restricted to this technical application. Further areas of application are bio-technology and medical technology, as well as generally the realm of technical ceramics in precision mechanics as well as machine and automotive construction. Dental ceramic products that can be made from the ceramics according to the invention are thus likewise the subject matter of the present invention. The above-mentioned properties of the ceramics according to the invention mean that they are suitable as dental material or as a dental product shaped with it or else as a component of dental material or of a dental product shaped with it. Preferred dental products are tooth root restorations such as, for example, tooth root constructions or tooth root posts, or dental bridges or dental crowns, especially skeleton ceramics and implant material. The high translucence of the ceramics of the present invention also allow their use as opto-ceramics.

Below, the invention will be described in greater detail on the basis of several examples without the scope of the invention being restricted by these. The following examples contain preferred embodiments and advantageous refinements of the invention. Further refinements and embodiments of the invention are contained in the subclaims.

EXAMPLES

Preliminary Remarks

The materials used are commercially available or can be made by means of well-known production methods.

The particle sizes were determined by means of laser diffraction and, after sintering, by means of a scanning electron microscope; the sintering shrinkage was determined by measuring the three spatial axes and the spatial diagonals of the cuboidal green compact and sintered body. The green and sintered densities were determined by means of the Archimedes principle, the three-point bend strength was determined according to the dental ceramic standard EN ISO 6872.

Example 1

Comparative Example

A $ZrO_2$ powder, stabilized with 3 mole-% of $Y_2O_3$ and having an average particle size of 620 nm, underwent cold isostatic compacting at 300 MPa at the minimum. The green density of this starting powder was 2.69 $g/cm^3$ on average. The compacted green compact was sintered in a bottom-loading furnace BL-1801 made by the Kendro company under the following conditions:
1. binder removal: 700° C. [1292° F.]
2. sintering: 1500° C. [2732° F.]

The three-point bend strength was 1149 MPa on average.

The sintering shrinkage was 24.7% on average, and the sintered density was 6.03 $g/cm^3$.

Example 2

Production of Nanoscale ZrO2 Powder by Means of a Plasma-Chemical Synthesis Method The nanoscale $ZrO_2$ powder was produced by adding particles of pure metals that were 30 μm to 40 μm in size or highly volatile metal compounds such as, for example, chlorides, directly to a low-temperature plasma that was generated by means of HF or UHF plasmatrons and that had a large plasma volume and a small flow rate (long contact time). 1757 grams of $ZrCl_4$ and 190 grams of $YCl_3.6\ H_2O$ were evaporated at 3000° K to 7000° K and theoretically yield 1 kg of nanoscale $ZrO_2$ (stabilized with 3 mole-% of $Y_2O_3$), whereby the fractionation of the powder still had to be carried out. The powder had an average particle size of 50 nm and a specific surface area of 26±2 $m^2/g$.

Example 3

Production of a Bimodal Metal Oxide Powder and of a Corresponding Ceramic

The nanoscale metal oxide powder from Example 2 was first deagglomerated by means of an ultrasound treatment. A surfactant was added to the surface-modified metal oxide powder from Example 1 with the nanoscale metal oxide powder from example 2 in an amount of 20% by weight (relative to the total weight of the bimodal metal oxide powder) in a rotary evaporator (ratio of powder mixture to solvent: 1:7). Subsequently, 3% by weight of binder was added to the mixture and mixed for 10 hours at 70° C. [158° F.]. Then the solvent was evaporated off and the powder mixture was dried at 60° C. [140° F.]. After that, the powder mixture was granulated and subjected to cold isostatic pre-compacting at 60 MPa. Subsequently, the green compact was ground up and final-compacted by a cold isostatic process at 300 MPa. The green compact thus obtained had a specific density of 4.14 $g/cm^3$ on average. The subsequent sintering was carried out as described in Example 1. The ceramic thus obtained was more translucent than in Example 1 and had the following additional properties:

The three-point bend strength was 1473 MPa on average.

The sintering shrinkage was 11.8% on average, and the sintered density was 6.08 g/cm$^3$.

The invention claimed is:

1. A ceramic or dental material or dental product comprising a ceramic, having a bimodal particle size distribution, whereby a first phase comprises a metal oxide having an average particle size of at least 250 nm, and a second phase comprises a metal oxide having an average particle size in a range of 25 nm to 250 nm; made from a bimodal metal oxide powder comprising (a) a first metal oxide powder, and (b) a second, nanoscale metal oxide powder; wherein the first metal oxide powder has a $d_{50}$ value in a range of 0.2 μm to 12 μm, and the second nanoscale metal oxide powder (b) has a $d_{50}$ value in a range of 10 nm to 200 nm; wherein the size ratio of the $d_{50}$ values of (a) to (b) lies at a maximum of 40 to 1; wherein the quantity ratio of (a) to (b) is in a range of 0.1:99.9 to 99.9:0.1; and wherein the metal oxide is selected from one member of the group consisting of $ZrO_2$, $HfO_2$, $TiO_2$, and $Al_2O_3$, undoped or optionally doped with one or more dopants selected from the group consisting of $CeO_2$, CaO, MgO, $Sc_2O_3$, and $Y_2O_3$.

2. The ceramic or dental material or dental product of claim 1, wherein the size ratio of the $d_{50}$ value of (a) to (b) lies between 12.4 and 40 to 1.

3. The ceramic or dental material or dental product of claim 1, wherein a metal oxide includes one or more dopants selected from the group consisting of $CeO_2$, CaO, MgO, $Sc_2O_3$, and $Y_2O_3$.

4. The ceramic or dental material or dental product according to claim 1, wherein the second, nanoscale metal oxide powder (b) comprises $ZrO_2$ and is stabilized with 0.5 mole % to 12 mole %, relative to the total amount of the second, nanoscale metal oxide powder (b), said one or more dopants.

5. The ceramic or dental material or dental product according to claim 4, wherein the dopant is 1 mole % to 5 mole % of $Y_2O_3$.

6. The ceramic or dental material or dental product according to claim 5, wherein the other metal oxide dopant is approximately 3 mole % of $Y_2O_3$.

7. The ceramic or dental material or dental product according to claim 1, wherein the second, nanoscale metal oxide powder (b) is made by means of a plasma synthesis method.

8. The ceramic or dental material or dental product according to claim 6, wherein the second, nanoscale metal oxide powder (b) has an average particle size of 50 nm.

9. The ceramic or dental material or dental product according to claim 6, wherein the second, nanoscale metal oxide powder (b) has an average particle size in a range of 15 nm to 100 nm.

10. The ceramic or dental material or dental product according to claim 9, wherein the second, nanoscale metal oxide powder (b) has an average particle size in a range of 40 nm to 50 nm.

11. The ceramic or dental material or dental product according to claim 1, wherein the bimodal metal oxide powder comprises 5% to 30% by weight of the second, nanoscale metal oxide powder (b), relative to the total weight of the bimodal metal oxide powder.

12. The ceramic or dental material or dental product of claim 11, wherein the bimodal metal oxide powder comprises 10% to 25% by weight of the second, nanoscale metal oxide powder (b), relative to the total weight of the bimodal metal oxide powder.

13. The ceramic or dental material or dental product of claim 12, wherein the bimodal metal oxide powder comprises about 20% by weight of the second, nanoscale metal oxide powder (b), relative to the total weight of the bimodal metal oxide powder.

14. The ceramic or dental material or dental product of claim 1, produced by a method wherein the bimodal metal oxide powder
   (C) undergoes cold isostatic (uniaxial) final compacting or else it is first pre-compacted and then undergoes final compacting or
   (C') is subjected to a pre-sintering at a sintering temperature in a range of 300° C. to 1100° C. for a sintering duration in a range of 0.5 to 8 hours.

15. The ceramic or dental material or dental product of claim 14, produced by a method wherein the bimodal metal oxide powder
   (C) undergoes cold isostatic compacting or
   (C') is subjected to a pre-sintering, and
   (D) the ceramic obtained in step (C) or the pre-sinter ceramic obtained in step (C') is subjected to sintering.

16. The ceramic or dental material or dental product of claim 15, produced by a method wherein the bimodal metal oxide powder
   (C) undergoes cold isostatic compacting or
   (C') is subjected to a pre-sintering;
   (E) the green compact ceramic obtained in step (C) or the pre-sinter ceramic obtained in step (C') undergoes a milling process; and
   (D') the milling ceramic obtained in step (E) is subjected to sintering.

* * * * *

UNITED STATES PATENT AND TRADEMARK OFFICE
CERTIFICATE OF CORRECTION

PATENT NO. : 7,608,552 B2 Page 1 of 1
APPLICATION NO. : 10/748084
DATED : October 27, 2009
INVENTOR(S) : Meyer et al.

It is certified that error appears in the above-identified patent and that said Letters Patent is hereby corrected as shown below:

On the title page item (73), Assignee Chemichl AG, Vaduz "(DE)" should be --(LI)--.

Signed and Sealed this

Ninth Day of March, 2010

David J. Kappos
*Director of the United States Patent and Trademark Office*